United States Patent
Roberts et al.

(10) Patent No.: US 11,660,291 B2
(45) Date of Patent: May 30, 2023

(54) IL-8 INHIBITORS FOR USE IN THE TREATMENT OF SOME SARCOMAS

(71) Applicants: Dompe' Farmaceutici S.P.A., Milan (IT); RESEARCH INSTITUTE AT NATIONWIDE CHILDREN'S HOSPITAL, Columbus, OH (US)

(72) Inventors: Ryan David Roberts, Grove City, OH (US); Laura Brandolini, L'Aquila (IT)

(73) Assignees: Dompe' Farmaceutici S.P.A., Milan (IT); Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 16/764,270

(22) PCT Filed: Oct. 23, 2018

(86) PCT No.: PCT/EP2018/078971
§ 371 (c)(1),
(2) Date: May 14, 2020

(87) PCT Pub. No.: WO2019/081470
PCT Pub. Date: May 2, 2019

(65) Prior Publication Data
US 2021/0361627 A1    Nov. 25, 2021

(30) Foreign Application Priority Data
Oct. 24, 2017   (EP) .................... 17198072

(51) Int. Cl.
*A61P 35/00*  (2006.01)
*A61K 31/18*  (2006.01)
*C07C 311/03*  (2006.01)
*C07C 311/08*  (2006.01)
*A61K 31/426*  (2006.01)
*A61K 33/243*  (2019.01)
*A61K 31/475*  (2006.01)
*A61K 31/519*  (2006.01)
*A61K 31/675*  (2006.01)
*A61K 31/704*  (2006.01)
*A61K 31/7048*  (2006.01)
*A61K 38/12*  (2006.01)

(52) U.S. Cl.
CPC ............ *A61K 31/426* (2013.01); *A61K 31/18* (2013.01); *A61K 31/475* (2013.01); *A61K 31/519* (2013.01); *A61K 31/675* (2013.01); *A61K 31/704* (2013.01); *A61K 31/7048* (2013.01); *A61K 33/243* (2019.01); *A61K 38/12* (2013.01); *A61P 35/00* (2018.01)

(58) Field of Classification Search
CPC ..... A61K 31/18; C07C 311/03; C07C 311/08; A61P 35/00
See application file for complete search history.

(56) References Cited

U.S. PATENT DOCUMENTS

| 10,660,909 B2 * | 5/2020 | Zebala ............... A61K 39/3955 |
| 2003/0096781 A1 | 5/2003 | Masood et al. |
| 2010/0136031 A1 | 6/2010 | Wicha et al. |
| 2017/0165363 A1 * | 6/2017 | Wirtz .................. C07K 16/244 |
| 2018/0296580 A1 | 10/2018 | Zebala et al. |

FOREIGN PATENT DOCUMENTS

| WO | 0024710 A1 | 5/2000 |
| WO | 2005090295 A2 | 9/2005 |
| WO | 2010031835 A2 | 3/2010 |
| WO | 2016057841 A1 | 4/2016 |
| WO | WO-2017/121838 A1 | 7/2017 |

OTHER PUBLICATIONS

Teicher, B., R. Bagley, C. Rouleau, A. Kruger, Y. Ren and L. Kurtzberg, "Characteristics of human Ewing/PNET sarcoma models", Ann Saudi Med. (2011); 31(2), pp. 174-182. (Year: 2011).*
Liotti et al., "Multiple anti-tumor effects of Reparixin on thyroid cancer", www.impactjournals.com/oncotarget/, Oncotarget, 2017, vol. 8, (No. 22), pp. 35946-35961.
PCT International Search Report and Written Opinion dated Jan. 18, 2019 for Intl. App. No. PCT/EP2018/078971, from which the instant application is based, 12 pgs.
Extended European Search Report dated Apr. 18, 2020 for related EP Application No. 17198072.5, 11 pgs.
Shih, Chun-Ho et al., Synergistic suppression of a disintegrin acurhagin-C in combination with AZD4547 and reparixin on termination development for human osteosarcoma MG-63 cell, vol. 492, No. 3 (Aug. 18, 2017), pp. 513-519.
Calvillo, L., et al., "Reduction of Ischemia-Reperfusion Injury in the Rat In Vivo by DF1681, an Inhibitor or Interleukin-8," Journal of the American College of Cardiology, vol. 37, No. Suppl. 02, (Feb. 1, 2001, XP001199808 Abstract, 1 pg.

* cited by examiner

*Primary Examiner* — Joseph R Kosack
*Assistant Examiner* — Sagar Patel
(74) *Attorney, Agent, or Firm* — Clark & Elbing LLP; Susan M. Michaud

(57) ABSTRACT

The present invention relates to IL-8 inhibitor compounds, preferably dual CXCR1/CXCR2 receptor inhibitors, useful in the treatment and/or prevention of some sarcomas, preferably in the treatment and/or prevention of osteosarcoma, Ewing sarcoma, rhabdomyosarcoma or lung metastasis associated thereof.

19 Claims, 5 Drawing Sheets

IL-8 INHIBITORS FOR USE IN THE TREATMENT OF SOME SARCOMAS

RELATED APPLICATIONS

This application is a 35 U.S.C. 371 national stage filing from International Application No. PCT/EP2018/078971, filed Oct. 23, 2018, which claims priority to European Application No. 17198072.5, filed Oct. 24, 2017, the teachings of which are incorporated herein by reference.

TECHNICAL FIELD

The present invention relates to IL-8 inhibitors for the prevention and/or treatment of some sarcomas, preferably osteosarcoma, Ewing sarcoma, rhabdomyosarcoma or lung metastasis associated thereof. The invention also relates to a pharmaceutical composition, product/kit comprising an IL-8 inhibitor with an IL-6 inhibitor or with a chemotherapeutic agent.

BACKGROUND ART

Bone and soft tissue sarcomas are a group of rare heterogeneous forms of cancer, which collectively account for approximately 1% of all malignancies diagnosed. Sarcomas represent a challenge to clinicians as they are rare and diagnosis is often delayed.

There are over one hundred different morphological subtypes of sarcoma. The most common types of bone sarcoma are osteosarcoma, chondrosarcoma, Ewing sarcoma and chordoma. Soft tissue sarcomas develop from soft tissue cells including smooth muscle cells (leiomyosarcomas), fat cells (liposarcomas), fibrous connective tissue (fibrosarcomas), skeletal muscles (rhabdomyosarcomas), synovium (synovial sarcomas), blood vessels (angiosarcomas), breast ducts (phyllodes tumours) and nerves (nerve sheath tumours).

Osteosarcoma (OS) is an aggressive malignant neoplasm that arises from primitive transformed cells of mesenchymal origin (and thus a sarcoma) and that exhibits osteoblastic differentiation and produces malignant osteoid.

It is the most common histological form of primary bone cancer and it is most prevalent in teenagers and young adults.

A complete radical, surgical, en bloc resection of the cancer is the treatment of choice in osteosarcoma. Although about 90% of patients are able to have limb-salvage surgery, complications, particularly infection, prosthetic loosening and non-union, or local tumor recurrence may cause the need for further surgery or amputation.

Standard therapy is a combination of limb-salvage orthopedic surgery when possible (or amputation in some cases) and chemotherapy.

Ewing sarcoma (ES) is a highly aggressive bone tumor with peak incidence in the adolescent population. It has a high propensity to metastasize, which is associated with dismal survival rates of approximately 25% (Satterfield, L. et al, Int. J. Cancer, 141: 2062-2075; 2017; Beverly A. Teicher et al, Ann Saudi Med., 31(2): 174-182; 2011).

Members of the Ewing sarcoma family of tumors (ESFT) contain tumor-associated translocations that give rise to oncogenic transcription factors, most commonly EWS/FLI1. EWS/FLI1 plays a dominant role in tumor progression by modulating the expression of hundreds of target genes. Here, the impact of EWS/FLI1 inhibition, by RNAi-mediated knockdown, on cellular signaling was investigated using mass spectrometry-based phosphoproteomics to quantify global changes in phosphorylation. This unbiased approach identified hundreds of unique phosphopeptides enriched in processes such as regulation of cell cycle and cytoskeleton organization. In particular, phosphotyrosine profiling revealed a large upregulation of STAT3 phosphorylation upon EWS/FLI1 knockdown. However, single-cell analysis demonstrated that this was not a cell-autonomous effect of EWS/FLI1 deficiency, but rather a signaling effect occurring in cells in which knockdown does not occur. Conditioned media from knockdown cells were sufficient to induce STAT3 phosphorylation in control cells, verifying the presence of a soluble factor that can activate STAT3. Cytokine analysis and ligand/receptor inhibition experiments determined that this activation occurred, in part, through an IL6-dependent mechanism. Taken together, the data support a model in which EWS/FLI1 deficiency results in the secretion of soluble factors, such as IL6, which activate STAT signaling in bystander cells that maintain EWS/FLI1 expression. Furthermore, these soluble factors were shown to protect against apoptosis (Jennifer L. Anderson et al; Mol Cancer Res; 12(12); 2014; Andrej Lissat et al, BMC Cancer, 15: 552; 2015).

Rhabdomyosarcoma (RMS) is an aggressive and highly malignant form of cancer that develops from skeletal (striated) muscle cells that have failed to fully differentiate. It is generally considered to be a disease of childhood, as the vast majority of cases occur in those below the age of 18.

Despite being a relatively rare cancer, it accounts for approximately 40% of all recorded soft-tissue sarcomas. RMS can occur in any site on the body, but is primarily found in the head, neck, orbit, genitourinary tract, genitals, and extremities. Treatment of rhabdomyosarcoma is a multidisciplinary practice involving the use of surgery, chemotherapy, radiation, and possibly immunotherapy. Surgery is generally the first step in a combined therapeutic approach. Resectability varies depending on tumor site, and RMS often presents in sites that don't allow for full surgical resection without significant morbidity and loss of function. Less than 20% of RMS tumors are fully resected with negative margins. Fortunately, rhabdomyosarcomas are generally chemosensitive, with approximately 80% of cases responding to chemotherapy.

Multi-agent chemotherapy is indicated for all patients with rhabdomyosarcoma. Before the use of adjuvant and neoadjuvant therapy involving chemotherapeutic agents, treatment solely by surgical means had a survival rate of <20%. Modern survival rates with adjuvant therapy are approximately 60-70%.

Metastasis kills patients with solid tumors. Nowhere is this more evident than in osteosarcoma. The deadly bone cancer osteosarcoma (OS) kills primarily through metastatic spread to lung. The mechanisms driving this lung tropism remain unknown. Whether patients present with grossly metastatic disease at diagnosis or metastases arise many years after completing therapy, patients with localized disease enjoy a relatively favorable 70% 5-year overall survival rate, while those with lung metastasis suffer an abysmal 15% 2-year survival (Allison D. C. et al; Sarcoma 2012, 704872; 2012).

Despite myriad attempts to augment therapy or to find novel treatments for metastatic disease, no treatment has significantly improved outcomes in over 40 years. Clearly, novel approaches will be needed in order to make inroads in the treatment of metastatic osteosarcoma (Luetke A. et al.; Cancer Treat. Rev. 40, 523-32; 2014). Large consortia of researchers in the field have suggested that further advances in treatment of osteosarcoma will not likely come without an improved understanding of the biology of metastasis and with the development of drugs targeting those pathways (Khanna C. et al; Clin Cancer Res; 20(16); 1-10; 2014). Some prior arts refer to the identification of the risk factors associated with the outcome in children with metastatic rhabdomyosarcoma (Oberlin O. et al; Journal of Clinical Oncology, 2008 May 10; 26(14): 2384-2389) and to the outcomes in children with rhabdomyosarcoma (RMS) and lung-only metastatic disease (J. Pediatr. Surg., 2005 January; 40(1):256-62).

A therapy which prevents the emergence of lung metastasis in children and adolescents with osteosarcoma would save the lives of more than 70% of those who currently die from their disease.

Interleukin-8 (IL-8; CXCL8) is considered a major mediator of PMN (Polymorphonuclear Neutrophils) recruitment and is involved in several pathologies including psoriasis, rheumatoid arthritis, chronic obstructive pulmonary disease and reperfusion injury in transplanted organ (Griffin et al, Arch Dermatol 1988, 124: 216; Fincham et al, J Immunol 1988, 140: 4294; Takematsu et al, Arch Dermatol 1993, 129: 74; Liu et al, 1997, 100:1256; Jeffery, Thorax 1998, 53: 129; Pesci et al, Eur Respir J. 1998, 12: 380; Lafer et al, Br J Pharmacol. 1991, 103: 1153; Romson et al, Circulation 1993, 67: 1016; Welbourn et al, Br J Surg. 1991, 78: 651; Sekido et al, Nature 1993, 365, 654). The biological activity of IL-8 is mediated by the interaction with two receptors, CXCR1 and CXCR2, belonging to the 7TM-GPCR family, that are expressed on the surface of human PMNs. While CXCR1 is selective, binding with high affinity only two chemokines, CXCL6 and IL-8, and showing a much higher affinity for IL-8 (Wolf et al, Eur J Immunol 1998, 28: 164), human CXCR2 is a more promiscuous receptor, binding a number of different cytokines and chemokines. Therefore, CXCR2 mediates the activity of a number of different biological molecules. Interleukin-6 (IL-6) is a pleiotropic cytokine with multiple functions in immune regulation, inflammation, and oncogenesis. Binding of IL-6 to the IL-6 receptor (IL-6R) induces homodimerization and recruitment of glycoprotein 130 (gp130), which leads to activation of downstream signaling.

Gp130 is part of the receptor signaling complexes for at least 8 cytokines (IL-6, IL-11, IL-27, LIF, CNTF, OSM, CT-1, and CLC). Ligand binding induces the association of gp130 with a cytokine-specific receptor-a chain, followed by the activation of downstream signaling cascades including JAK/STAT, RAS/RAF/MAPK, and PI3K/AKT pathways. It has been shown that phosphorylation of gp130 at Ser782 downregulates cell surface expression of gp130. As a ubiquitously expressed receptor, gp130 is involved in a wide range of important biologic processes including inflammation, autoimmunity, cancer, stemcell maintenance, and embryonic development (Mol Cancer Ther; 12(6); 937-49; 2013).

SUMMARY OF THE INVENTION

The present inventors have surprisingly found that inhibition of IL-8 is able to reduce or prevent the occurrence of lung metastasis associated with osteosarcoma, Ewing sarcoma or rhabdomyosarcoma. In particular, the combination of an IL-8 inhibitor with an IL-6 inhibitor is resulted more effective.

The present inventors have also surprisingly found that an IL-8 inhibitor is useful in the prevention and/or treatment of the primary tumor osteosarcoma, Ewing sarcoma or rhabdomyosarcoma. Preferably, when IL-8 inhibitor is combined with a chemotherapeutic agent.

Accordingly, a first object of the present invention is an IL-8 inhibitor, preferably an antibody or a small molecular weight molecule, preferably a CXCR1 inhibitor, more preferably a dual CXCR1/CXCR2 inhibitor, for use in the prevention and/or treatment of bone and soft tissue sarcomas, preferably osteosarcoma, Ewing sarcoma, rhabdomyosarcoma or lung metastasis associated thereof.

The second object of the present invention is the use of said IL-8 inhibitor as defined above, for the preparation of a medicament for the prevention and/or treatment of bone and soft tissue sarcomas, preferably osteosarcoma, Ewing sarcoma, rhabdomyosarcoma or lung metastasis associated thereof.

The third object of the present invention is a method for the prevention and/or treatment of bone and soft tissue sarcomas, preferably osteosarcoma, Ewing sarcoma, rhabdomyosarcoma or lung metastasis associated thereof comprising the step of administering to a subject in need thereof a therapeutically effective amount of said IL-8 inhibitor.

The fourth object of the invention is a pharmaceutical composition for the prevention and/or treatment of bone and soft tissue sarcomas, preferably osteosarcoma, Ewing sarcoma, rhabdomyosarcoma or lung metastasis associated thereof comprising an IL-8 inhibitor according to the invention and pharmaceutically acceptable excipients and/or diluents.

According to one preferred embodiment, said pharmaceutical composition for the prevention and/or treatment of bone and soft tissue sarcomas, preferably osteosarcoma, Ewing sarcoma, rhabdomyosarcoma or lung metastasis associated thereof, more preferably lung metastasis, further comprises at least one IL-6 inhibitor and/or at least one gp130 inhibitor.

According to another preferred embodiment, said pharmaceutical composition for the prevention and/or treatment of bone and soft tissue sarcomas, preferably osteosarcoma, Ewing sarcoma, rhabdomyosarcoma or lung metastasis associated thereof, more preferably the primary tumor, further comprises at least one chemotherapeutic agent.

The fifth and sixth object of the present invention are a product or a kit for use in the treatment and/or prevention of bone and soft tissue sarcomas, preferably osteosarcoma, Ewing sarcoma, rhabdomyosarcoma or lung metastasis associated thereof, comprising an IL-8 inhibitor as defined above and one or more pharmaceutically active compounds for simultaneous, separate or sequential use.

DETAILED DESCRIPTION OF THE INVENTION

Figure 1:
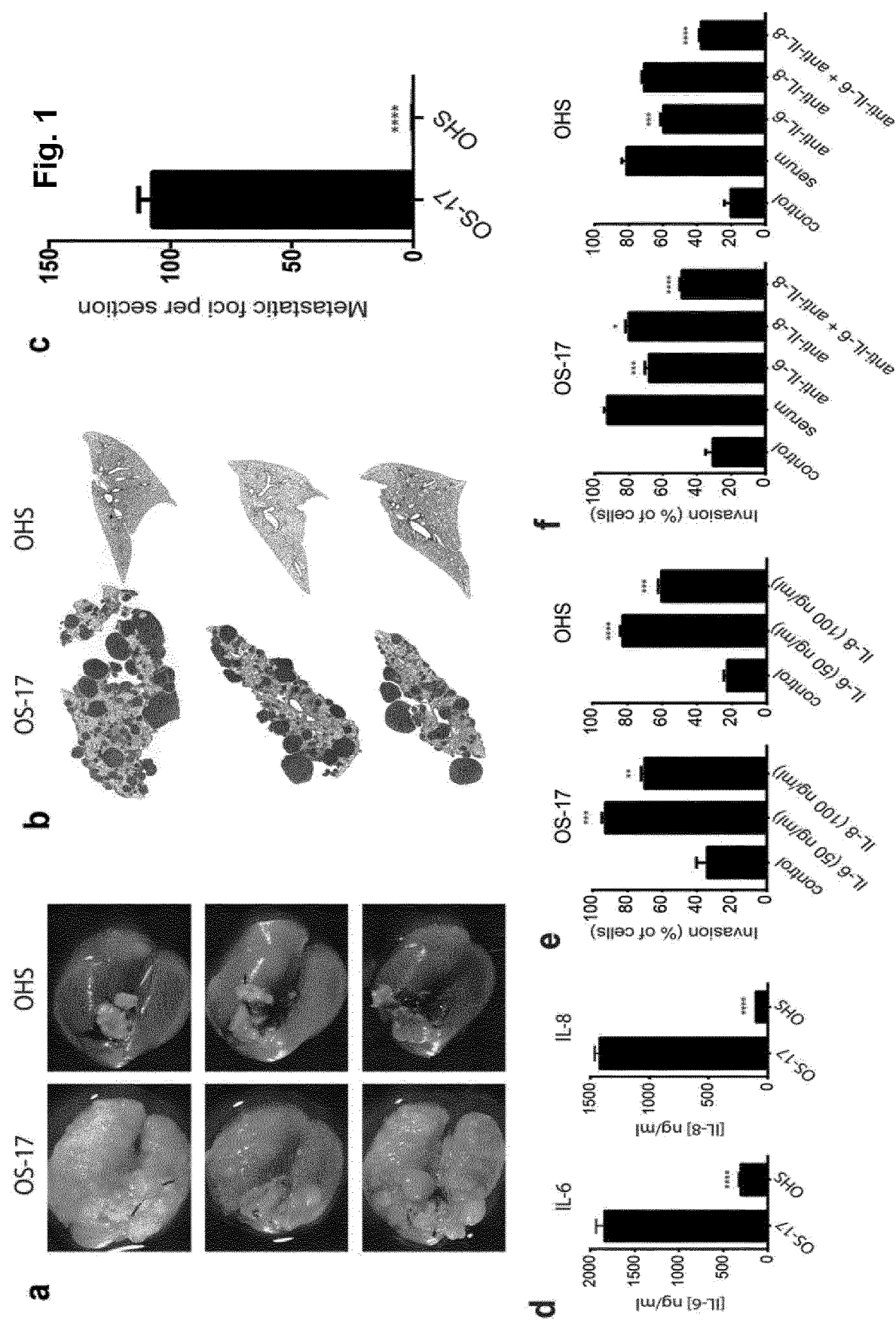
FIG. 1 shows IL6 and IL8 expression correlate with metastatic efficiency and metastatic behaviors in xenograft models of metastasis. CB17-SCID mice inoculated with $1 \times 10^6$ OS cells were euthanized 49 days after innoculation. a) Gross appearance of lung blocks taken from those mice suggests markedly greater efficiency of colonization by OS-17 relative to the other cell lines. b) H&E stains from sections of paraffin-embedded left lobes were counted to quantify the number of metastases per section. c) Quantification reveals significantly higher numbers of metastases in the OS-17 sections relative to OHS. d) Determination of IL-6 and Il-8 concentrations in 72 hour supernatants from cultures of each cell line reveals significant expression of both cytokines in the metastatic OS-17 cells relative to either non-metastatic cell line. e)-f) Evaluation of capacity to respond to IL-6 and IL-8 signals using transwell migration assay.

As it will be disclosed in details in the Experimental Section, the present inventors have found that molecules acting as inhibitors of IL-8 activity have therapeutic efficacy in animal models of sarcoma. Furthermore, the present inventors have also found that IL-8 inhibition is able to counteract the onset of lung metastasis. In particular, the combined IL-8 and IL-6 inhibition prevents metastasis.

Accordingly, a first object of the present invention is an IL-8 inhibitor for use in the treatment and/or prevention of bone and soft tissue sarcomas, preferably osteosarcoma, Ewing sarcoma or rhabdomyosarcoma.

According to a preferred embodiment, said IL-8 inhibitor is for use in the prevention and/or treatment of lung metastasis associated to osteosarcoma, Ewing sarcoma or rhabdomyosarcoma.

The term "IL-8-inhibitor" according to the present application refers to any compound able to inhibit, partially or totally, the biological activity of IL-8. Such a compound can act by decreasing the expression or activity of IL-8 or by inhibiting the triggering of the intracellular signaling activated by the IL-8 receptors. It is preferred that said IL-8 inhibitor is able to inhibit at least 50%, preferably at least 60%, of the chemotaxis induced by IL-8 in PMNs at a concentration equal or below 500 nM, preferably below 100 nM.

According to a preferred embodiment, the IL-8 inhibitor of all the objects of the present invention inhibits the activity of IL-8 mediated by CXCR1 receptor or mediated by both CXCR1 and CXCR2 receptors.

Preferably, according to this embodiment, said IL-8 inhibitor is either an allosteric inhibitor or an orthosteric antagonist of CXCR1 receptor or of both CXCR1 and CXCR2 receptors.

Preferably, said IL-8 inhibitor is selective for CXCR1 receptor or is equally potent towards CXCR1 and CXCR2 receptors.

By "selective for CXCR1" according to the present invention it is meant a compound that shows an $IC_{50}$ value at least 2, preferably 3, logs higher toward CXCR1 than towards CXCR2. (Bertini R. et al., Proc. Nat. Acad. Sci. USA (2004), 101 (32), pp. 11791-11796).

By "equally potent towards CXCR1 and CXCR2" it is meant a compound that shows an $IC_{50}$ value in the range 10 picomolar $(10^{-11}M)$–1 micromolar $(10^{-6}M)$ towards CXCR1 and CXCR2. (Bertini R. et al., Br. J. Pharm. (2012), 165, pp. 436-454). More preferably, the IL-8 inhibitor according to the invention has an $IC_{50}$ value towards CXCR1 receptor in the low nanomolar range, preferably in the range 0.02-5 nanomolar.

According to a preferred embodiment, also in combination with the preceding embodiment, said IL-8 inhibitor is selected from small molecular weight molecules and antibodies, more preferably it is a small molecular weight molecule.

IL-8 inhibitors according to the above definition, able to inhibit the activity of IL-8 mediated by CXCR1 receptor or mediated by both CXCR1 and CXCR2 receptors, are known in the art.

Preferred IL-8 inhibitors according to the invention are selected from 1,3-thiazol-2-ylaminophenylpropionic acid derivatives, 2-phenyl-propionic acid derivatives and their pharmaceutically acceptable salts.

Among the above compounds, said 1,3-thiazol-2-ylaminophenylpropionic acid derivative is preferably a compound of formula (I):

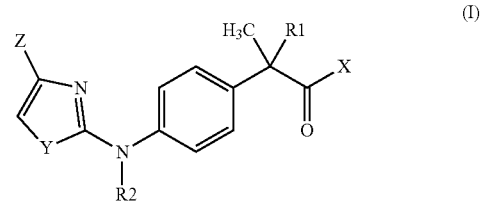

or a pharmaceutically acceptable salt thereof, wherein

R1 is hydrogen or $CH_3$;

R2 is hydrogen or linear $C_1$-$C_4$ alkyl, preferably it is hydrogen;

Y is a heteroatom selected from S, O and N; preferably it is S;

Z is selected from halogen, linear or branched $C_1$-$C_4$ alkyl, $C_2$-$C_4$ alkenyl, $C_2$-$C_4$ alkynyl, $C_1$-$C_4$ alkoxy, hydroxyl, carboxyl, $C_1$-$C_4$ acyloxy, phenoxy, cyano, nitro, amino, $C_1$-$C_4$ acylamino, halo $C_1$-$C_3$ alkyl, halo $C_1$-$C_3$ alkoxy, benzoyl, linear or branched $C_1$-$C_8$ alkanesulfonate, linear or branched $C_1$-$C_8$ alkanesulfonamide, linear or branched $C_1$-$C_8$ alkylsulfonylmethyl; preferably it is trifluoromethyl;

X is OH or a residue of formula NHR$_3$; wherein R$_3$ is selected from:
hydrogen, hydroxyl, linear or branched C$_1$-C$_6$ alkyl, C$_3$-C$_6$ cycloalkyl, C$_2$-C$_6$ alkenyl, C$_1$-C$_5$ alkoxy, or C$_1$-C$_6$ phenylalkyl, wherein alkyl, cycloalkyl or alkenyl group can be substituted by a COOH residue
a residue of formula SO$_2$R4 wherein R4 is C$_1$-C$_2$ alkyl, C$_3$-C$_6$ cycloalkyl, C$_1$-C$_3$ haloalkyl.

Preferably, in the above compounds X is OH.

Among the above compounds, particularly preferred are compounds of said formula (I) or pharmaceutically acceptable salts thereof, wherein:
R1 is CH$_3$;
R2 is hydrogen or linear C$_1$-C$_4$ alkyl, preferably it is hydrogen;
Y is a heteroatom selected from S, O and N; preferably it is S;
Z is selected from halogen, linear or branched C$_1$-C$_4$ alkyl, C$_2$-C$_4$ alkenyl, C$_2$-C$_4$ alkynyl, C$_1$-C$_4$ alkoxy, hydroxyl, carboxyl, C$_1$-C$_4$ acyloxy, phenoxy, cyano, nitro, amino, C$_1$-C$_4$ acylamino, halo C$_1$-C$_3$ alkyl, halo C$_1$-C$_3$ alkoxy, benzoyl, linear or branched C$_1$-C$_8$ alkanesulfonate, linear or branched C$_1$-C$_8$ alkanesulfonamides, linear or branched C$_1$-C$_8$ alkylsulfonylmethyl; preferably it is trifluoromethyl;
X is OH or a residue of formula NHR$_3$; wherein R$_3$ is selected from:
hydrogen, hydroxyl, linear or branched C$_1$-C$_6$ alkyl, C$_3$-C$_6$ cycloalkyl, C$_2$-C$_6$ alkenyl, C$_1$-C$_5$ alkoxy, or C$_1$-C$_6$ phenylalkyl, wherein alkyl, cycloalkyl or alkenyl group can be substituted by a COOH residue
a residue of formula SO$_2$R4 wherein R4 is C$_1$-C$_2$ alkyl, C$_3$-C$_6$ cycloalkyl, C$_1$-C$_3$ haloalkyl.

Preferably, in these compounds X is OH.

Among the above compounds, particularly preferred are also compounds of said formula (I) or pharmaceutically acceptable salts thereof, wherein
R1 is hydrogen;
R2 is hydrogen or linear C$_1$-C$_4$ alkyl, preferably it is hydrogen;
Y is a heteroatom selected from S, O and N; preferably it is S;
Z is selected from halogen, linear or branched C$_1$-C$_4$ alkyl, C$_2$-C$_4$ alkenyl, C$_2$-C$_4$ alkynyl, C$_1$-C$_{O4}$ alkoxy, hydroxyl, carboxyl, C$_1$-C$_4$ acyloxy, phenoxy, cyano, nitro, amino, C$_1$-C$_4$ acylamino, halo C$_1$-C$_3$ alkyl, halo C$_1$-C$_3$ alkoxy, benzoyl, linear or branched C$_1$-C$_8$ alkanesulfonate, linear or branched C$_1$-C$_8$ alkanesulfonamides, linear or branched C$_1$-C$_8$ alkylsulfonylmethyl; preferably it is selected from trifluoromethyl;
X is OH or a residue of formula NHR$_3$; wherein R$_3$ is selected from
hydrogen, hydroxyl, linear or branched C$_1$-C$_6$ alkyl, C$_3$-C$_6$ cycloalkyl, C$_2$-C$_6$ alkenyl, C$_1$-C$_5$ alkoxy, or C$_1$-C$_6$ phenylalkyl, wherein alkyl, cycloalkyl or alkenyl group can be substituted by a COOH residue;
a residue of formula SO$_2$R4 wherein R4 is C$_1$-C$_2$ alkyl, C$_3$-C$_6$ cycloalkyl, C$_1$-C$_3$ haloalkyl. More preferably X is NH$_2$.

Preferably, in the above compounds X is OH.

Among the above compounds, particularly preferred are also compounds of said formula (I) or pharmaceutically acceptable salts thereof, wherein:
R1 is hydrogen or CH$_3$;
R2 is hydrogen or linear C$_1$-C$_4$ alkyl, preferably it is hydrogen;
Y is a heteroatom selected from S, O and N; preferably it is S;
Z is selected from linear or branched C$_1$-C$_4$ alkyl, linear or branched C$_1$-C$_4$ alkoxy, halo C$_1$-C$_3$ alkyl and halo C$_1$-C$_3$ alkoxy; preferably it is selected from methyl, methoxy, trifluoromethoxy, trifluoromethyl, more preferably it is trifluoromethyl;
X is OH.

Among the above compounds, particularly preferred are also compounds of said formula (I) or pharmaceutically acceptable salts thereof, wherein:
R1 is CH$_3$;
R2 is hydrogen or linear C$_1$-C$_4$ alkyl, preferably it is hydrogen.
Y is a heteroatom selected from S, O and N; preferably it is S.
Z is selected from linear or branched C$_1$-C$_4$ alkyl, linear or branched C$_1$-C$_4$ alkoxy, halo C$_1$-C$_3$ alkyl and halo C$_1$-C$_3$ alkoxy; preferably it is selected from methyl, methoxy, trifluoromethoxy, trifluoromethyl, more preferably it is trifluoromethyl.

Among the above compounds, particularly preferred are also compounds of said formula (I) or pharmaceutically acceptable salts thereof, wherein
R1 is hydrogen;
X is OH;
R2 is hydrogen or linear C$_1$-C$_4$ alkyl, preferably it is hydrogen;
Y is a heteroatom selected from S, O and N; preferably it is S;
Z is selected from linear or branched C$_1$-C$_4$ alkyl, linear or branched C$_1$-C$_4$ alkoxy, halo C$_1$-C$_3$ alkyl and halo C$_1$-C$_3$ alkoxy; preferably it is trifluoromethyl.

Preferably, in all of the above compounds of formula (I) wherein R1 is hydrogen, the chiral carbon atom of the phenylpropionic group is in the S configuration.

Particularly preferred are compounds of formula (I) according to the invention selected from 2-methyl-2-(4-{[4-(trifluoromethyl)-1,3-thiazol-2-yl]amino}phenyl)propanoic acid (herein indicated also as DF2726Y) and pharmaceutically acceptable salts thereof, preferably its sodium salt (herein indicated also as DF2726A) and 2-(4-{[4-(trifluoromethyl)-1,3-thiazol-2-yl]amino}phenyl)propanoic acid and pharmaceutically acceptable salts thereof, preferably (2S)-2-(4-{[4-(trifluoromethyl)-1,3-thiazol-2-yl]amino}phenyl) propanoic acid (also known as DF2755Y) and its sodium salt, also known as DF2755A.

Compounds of formula (I) are disclosed in WO2010/031835, which also discloses their method of synthesis, their activity as IL-8 inhibitors as well as their use in the treatment of IL-8 dependent pathologies such as transient cerebral ischemia, bullous pemphigoid, rheumatoid arthritis, idiopathic fibrosis, glomerulonephritis and damages caused by ischemia and reperfusion.

Among the above IL-8 inhibitors, said 2-phenyl-propionic acid derivative is preferably a compound of formula (II):

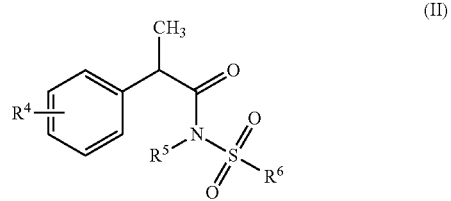

or a pharmaceutically acceptable salt thereof, wherein $R^4$ is linear or branched $C_1$-$C_6$ alkyl, benzoyl, phenoxy, trifluoromethanesulfonyloxy; preferably it is selected from benzoyl, isobutyl and trifluoromethanesulfonyloxy. Also, according to a preferred embodiment $R^4$ is in position 3 or 4 on the phenyl ring, more preferably it is 3-benzoyl, 4-isobutyl or 4-trifluoromethanesulfonyloxy.

$R^5$ is H or linear or branched $C_1$-$C_3$ alkyl, preferably it is H.

$R^6$ is linear or branched $C_1$-$C_6$ alkyl or trifluoromethyl; preferably, it is a linear or branched $C_1$-$C_6$ alkyl, more preferably it is $CH_3$.

Among the above compounds, preferred are compounds of formula (II) or a pharmaceutically acceptable salts thereof, wherein:

$R^4$ is $C_1$-$C_6$ alkyl or benzoyl; preferably it is in positions 3 and 4, more preferably, it is 3-benzoyl or 4-isobutyl.

$R^5$ is H or linear or branched $C_1$-$C_3$ alkyl, preferably it is H, $R^6$ is linear or branched $C_1$-$C_6$ alkyl or trifluormethyl; preferably it is a linear or branched $C_1$-$C_6$ alkyl, more preferably it is $CH_3$.

Among the above compounds, preferred are compounds of formula (II) or a pharmaceutically acceptable salts thereof, wherein:

$R^4$ is trifluoromethanesulfonyloxy, preferably 4-trifluoromethanesulfonyloxy, $R^5$ is H or linear or branched $C_1$-$C_3$ alkyl, preferably it is H, $R^6$ is linear or branched $C_1$-$C_6$ alkyl or trifluormethyl; preferably it is a linear or branched $C_1$-$C_{16}$ alkyl, more preferably it is $CH_3$ Among the above compounds, also preferred are compounds of formula (III):

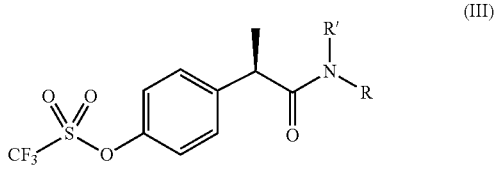

(III)

or a pharmaceutically acceptable salts thereof, wherein

R' is hydrogen;

R is a residue of formula $SO_2Ra$ wherein Ra is linear or branched $C_1$-$C_{04}$ alkyl or halo $C_1$-$C_3$ alkyl, preferably it is $CH_3$.

Preferably, in the above compound of formula (II) or (III), the chiral carbon atom of the phenylpropionic group is in the R configuration.

Particularly preferred compounds of formula (II) according to the invention are selected from R-(−)-2-(4-isobutylphenyl)propionyl methansulfonamide (also known as Reparixin) and pharmaceutically acceptable salts thereof. Preferably, said compound is the lysine in situ salt of R(−)-2-(4-isobutylphenyl)propionyl methansulfonamide (herein indicated also as DF1681B).

Further particularly preferred compounds of formula (II) or (III) according to the invention are 2-(4-trifluoromethanesulfonyloxy)phenyl]-N-methanesulfonyl propionamide and pharmaceutically salts thereof, preferably its sodium salt preferably R(−)-2-(4-trifluoromethanesulfonyloxy)phenyl]-N-methanesulfonyl propionamide (also known as DF2156Y) and its sodium salt (also known as Ladarixin or DF2156A).

IL-8 inhibitors of formula (II) and (III) are disclosed in WO0024710 and WO2005/090295, that also disclose their method of synthesis, their activity as IL-8 inhibitors as well as their use as inhibitors of neutrophils chemotaxis and degranulation induced by IL-8 and in the treatment of IL-8 dependent pathologies such as psoriasis, ulcerative colitis, melanoma, chronic obstructive pulmonary diseases (COPD), bullous pemphigoid, rheumatoid arthritis, idiopathic fibrosis, glomerulonephritis and damages caused by ischemia and reperfusion.

The second object of the present invention is the use of an IL-8 inhibitor for the preparation of a medicament for the treatment and/or prevention of bone and soft tissue sarcomas, preferably osteosarcoma, Ewing sarcoma or rhabdomyosarcoma.

According to a preferred embodiment of the present invention, said medicament is for the treatment and/or prevention of lung metastasis associated to bone and soft tissue sarcomas, preferably osteosarcoma, Ewing sarcoma or rhabdomyosarcoma.

The third object of the present invention is a method for the treatment and/or prevention of bone and soft tissue sarcomas, preferably osteosarcoma, Ewing sarcoma or rhabdomyosarcoma, comprising the step of administering to the subject in need thereof, a therapeutically effective amount of an IL-8 inhibitor, as defined above.

According to a preferred embodiment of the present invention, said method is for the treatment and/or prevention of lung metastasis associated to bone and soft tissue sarcomas, preferably osteosarcoma, Ewing sarcoma or rhabdomyosarcoma.

As used herein, a "therapeutically effective amount" refers to an amount sufficient to achieve treatment or prevention of the disease. Determination of the effective amounts is well within the capability of those skilled in the art based upon the achievement of a desired effect. An effective amount will depend on factors including, but not limited to, the weight of a subject and/or the degree of the disease or unwanted condition from which a subject suffers.

The terms "treatment" and "prevention" as used herein refer to the eradication/amelioration or prevention/delay in onset, respectively, of the disorder being treated or of one or more of the symptoms associated thereof, notwithstanding the fact that the patient may still be afflicted with the underlying disorder.

The fourth object of the present invention is a pharmaceutical composition comprising an IL-8 inhibitor as defined above, for use in the treatment and/or prevention of bone and soft tissue sarcomas, preferably osteosarcoma, Ewing sarcoma, rhabdomyosarcoma or lung metastasis associated thereof in association with pharmaceutically acceptable excipients and/or diluents.

According to one preferred embodiment, said pharmaceutical composition for the prevention and/or treatment of bone and soft tissue sarcomas, preferably osteosarcoma, Ewing sarcoma, rhabdomyosarcoma or lung metastasis associated thereof, more preferably lung metastasis, further comprises at least one IL-6 inhibitor and/or at least one gp130 inhibitor.

The term "IL-6 inhibitor" according to the present application refers to any compound able to inhibit, partially or totally, the biological activity of IL-6.

The term "gp130 inhibitor" according to the present application refers to any compound able to inhibit, partially or totally, the biological activity of gp130.

According to another preferred embodiment, said pharmaceutical composition for the prevention and/or treatment of bone and soft tissue sarcomas, preferably osteosarcoma, Ewing sarcoma, rhabdomyosarcoma or lung metastasis associated thereof, more preferably the primary tumor, further comprises at least one chemotherapeutic agent.

The fifth object of the present invention is a product or kit comprising: A) an IL-8 inhibitor as defined above for use in the treatment and/or prevention of bone and soft tissue sarcomas, preferably osteosarcoma, Ewing sarcoma, rhabdomyosarcoma or lung metastasis associated thereof or a pharmaceutical composition as defined above, and B) at least one IL-6 inhibitor and/or at least one gp130 inhibitor, A) and B) being two separate formulations for simultaneous, separate or sequential use. Preferably, for use in the treatment and/or prevention of lung metastasis associated to osteosarcoma, Ewing sarcoma or rhabdomyosarcoma.

According to one preferred embodiment, said gp130 inhibitor is selected from the group comprising 2-(7-Fluoropyrrolo[1,2-a]quinoxalin-4-yl) 2-pyrazinecarboxylic acid hydrazide (SC144), Raloxifene and (4R)-3-((2S,3S)-3-hydroxy-2-methyl-4-methylenenonanoyl)-4-isopropyldihydrofuran-2(3H)-one (LMT-28) (Tae-Hwe Heo et al.; Oncotarget, Vol. 7, No. 13, 15460-15473; 2016).

According to one preferred embodiment, said IL-6 inhibitor is selected from the group comprising SC144, Vobarilizumab, Siltuximab, Sirukumab, Olokizumab, Clazakizumab, MAb 1339, Tocilizumab and Sarilumab (Tae-Hwe Heo et al.; Oncotarget, Vol. 7, No. 13, 15460-15473; 2016).

Preferably, said IL-6 inhibitor is SC144.

The sixth object of the present invention is a product or kit comprising: A') an IL-8 inhibitor as defined above for use in the treatment and/or prevention of bone and soft tissue sarcomas, preferably osteosarcoma, Ewing sarcoma, rhabdomyosarcoma or lung metastasis associated thereof or a pharmaceutical composition as defined above, and B') at least one chemotherapeutic agent, A') and B') being two separate formulations for simultaneous, separate or sequential use. Preferably, for use in the treatment and/or prevention of the primary tumor osteosarcoma, Ewing sarcoma or rhabdomyosarcoma.

Preferably, said chemotherapeutic agent is selected from the group comprising doxorubicin, cisplatin, methotrexate, ifosfamide, epirubicin, etoposide, cyclophosphamide, vincristine and actinomycin D.

For the purpose of the present invention, the inhibitors of IL-8 according to the present invention are formulated in pharmaceutical compositions suitable for use by oral formulation, such as tablets, capsules, syrups, preferably in the form of controlled release formulations, or by parenteral administration, preferably in the form of sterile solutions suitable for intravenous or intramuscular administration. The pharmaceutical compositions can be prepared according to conventional methods, for example as disclosed in Remington, "The Science and Practice of Pharmacy", 21st ed. (Lippincott Williams and Wilkins).

The average daily dose depends on several factors such as the severity of the disease, the condition, age, sex and weight of the patient. The dose will vary generally from 1 to 1500 mg of compounds of formula (I) per day optionally divided in multiple administrations.

The invention will be further illustrated in greater details in the following experimental section.

Experimental Section

Methods

Cell lines and primary cell cultures. OS-17 was derived from the OS-17 xenograft and obtained from the Istituti Ortopedici Rizzoli, Bologna, Italy. OS-25 and OHS were a gift from Dr. Fodstad's lab at the Radium Hospital in Oslo. All were maintained in RPMI (Corning #10-040-CV) supplemented with 10% FBS (Atlanta Biologicals #S11150H). 143B and K7M2 cells were obtained from ATCC (ATCC #CRL¬8303 and #CRL2836) and grown in DMEM (Corning #10-013-CV) supplemented with 10% FBS. OSCA-8 and OSCA-16 were provided by Jamie Modiano and the University of Minnesota and grown in RPMI with 10% FBS. Lung smooth muscle cells (ATCC #PCS-130-10) were grown in vascular cell basal medium (ATCC #PCS-100-030) supplemented with the vascular smooth muscle cell growth kit (ATCC #PCS-100-042). HUVEC cells (Lonza CC-2517) were grown in endothelial basal medium (Lonza #CC-5036) supplemented with the EGM-plus single quote (Lonza #CC-4542). Human lung fibroblasts (ATCC #PCS-201-013) were grown in EMEM (ATCC #30-2003) supplemented with 10% FBS. HBEC3-KT cells (ATCC #CRL-4051) were grown in airway epithelial cell basal medium (ATCC #PCS-300-030) supplemented with the bronchial epithelial cell growth kit (ATCC #PCS-300-040). Macrophages were derived from monocytes isolated from whole blood (obtained through an institutional IRB-approved protocol for the procurement of fresh human blood) using a CD14 magnetic bead selection system (Miltenyi #130-050-201) followed by 72 hours of culture in XVIVO serum-free medium (Lonza #04-380Q) supplemented daily with 20 ng/ml of recombinant human M-CSF (BioLegend #574802). For co-culture experiments, cultures within each group (co-culture and related monocultures) were performed using a 1:1 mixture of the two corresponding growth media to control for differences in media components.

IL-6 and IL-8 ELISA. Cell-free supernatants from 72-hour cultures of each cell line performed in 24-well plates were evaluated for IL-6 and IL-8 concentrations using R&D DuoSet ELISA Development Kits (#DY206 and #DY208), used according to manufacturer recommendations.

Scratch ("wound healing") assays. Monolayer cultures of OS-17 or OHS cell lines were disrupted using an Essen Incucyte WoundMaker (Essen Cell Migration Kit #4493). Individual wells were then serially imaged using an Essen Incucyte Zoom. Analysis was performed and wound width quantified using Essen's Integrated Cell Migration Analysis Module (Essen #9600-0012).

Transwell migration and invasion assays. $1 \times 10^4$ OS cells were plated into transwell inserts (either Falcon #353097 for migration or Corning #354483 for Matrigel invasion assays) containing appropriate chemotactic factors. After 24 hours of incubation, transwells were drained and upper chambers/membrane upper surfaces scraped using a polyester swab. Membranes were stained using a Dif-Quik Stain Set (Siemens #B4132-1A) and dried, then imaged on an inverted microscope. Cells were quantified using Adobe Photoshop counting tools. For experiments involving IL-6 and IL-8 chemotaxis, media contained 1% FBS in both chambers, with recombinant protein added to the bottom chamber to make 50 ng/ml IL6 (BioLegend #570804) or 100 ng/ml IL-8 (BioLegend #574204). For experiments using serum as a chemoattractant, top chambers contained RPMI only, while bottom chambers contained 1% or 2.5% serum. Where noted, 20 ug/ml of neutralizing antibodies to either IL6 (Abcam #AB6672), IL-8 (Abcam #AB18672), or both were added to both upper and lower chambers. In experiments testing the ability of small molecules to block serum-induced migration/invasion, 1 µM sc144 (Sigma #SML0763) and/or 100 nM DF2156A (Dompe Pharmaceuticals, Milan, Italy) was added to the media.

OS cell proliferation. Cells plated at 20% confluence were cultured in growth medium as above containing inhibitors as noted in each figure. Proliferation was serially quantified using an Essen Biosciences Incucyte Zoom over the time period noted in each figure.

Colony formation. $1\times10^4$ OS cells were plated in 1.5 ml of 0.5% soft agar (Lonza SeaPlaque GTG Agarose, #50111 in Gibco powdered RPMI #430-1800) over a 1.5 ml bed of 1% soft agar in 6 well plates, then covered with 500 ml RPMI. Where noted, drug was added to the RPMI layer sufficient to generate the stated concentration when diffused throughout both media and agar.

Xenograft survival studies. 6-8 week old CB17-SCID (Envigo C.B-17/IcrHsd-Prkdcscid) mice inoculated via tail vein with $1\times10^6$ OS-17 cells (day 0) received daily injections of sc144 (10 mg/kg SC once daily, Sigma #SML0763), DF2156A (30 mg/kg IP once daily), or both beginning 24 hours after inoculation. sc144 was prepared by dissolving with warming in DMSO to make a 40 mg/kg solution, which was immediately diluted to 2 mg/kg using 40% propylene glycol/1% Tween-20 in water. An average 20 g mouse received 100 ul per dose. Doses of sc144 were prepared fresh each day. DF2156A was prepared by dissolving in PBS to create a 6 mg/ml solution for similar 100 ul doses in a 20 g mouse. Treatments continued for 42 days, then stopped. Mice were monitored with twice weekly weights and enhanced body condition scoring (eBCS (28)). Mice demonstrating >10% weight loss or eBCS <8 were euthanized and tissues harvested, lungs insufflated, fixed in 10% neutral buffered formalin, then embedded and processed as above. Mice not demonstrating metastatic disease burden (presumably dying from other causes) are censored in the survival analysis. This includes 2 mice receiving combined therapy, one receiving sc144, and one control mouse.

Timepoint treatment studies. 6-8 week old CB17-SCID mice were inoculated with $1\times10^6$ 143 B, OSCA-8, OSCA-16, or K7M2 cells (for K7M2 cells, immunocompetent Balb/c mice were used). 24 hours after inoculation, mice began treatment with daily sc144 and/or DF2156A, which continued for 42 days as above. Mice were then observed as above until one mouse from any given cell line group reached endpoint. If lungs taken from this sentinel mouse showed signs of metastatic disease, all mice from that group were euthanized, lungs harvested, insufflated, fixed, embedded, and stained. A central section of the left lobe stained with H&E was reviewed using microscopy to count metastatic lesions by an experienced, blinded reviewer.

Statistical Analysis. Data were graphed and analyzed using Graphpad Prism 7. The specific statistical tests used and comparisons made are identified in the caption for each figure. Where necessary, adjustment for multiple comparisons was performed using the Benjamini-Hochberg method to control for a false discovery rate of 0.05.

Example 1

Production of IL-6 and IL-8 Correlates with Metastatic Potential in Murine Xenograft Models of Lung Colonization.

The present inventors tested a panel of osteosarcoma cell lines for their ability to colonize mouse lung. The present inventors found that OS-17 cells, when introduced into circulation via tail vein, develop metastatic loci with very high efficiency, while OHS cell lines demonstrate much lower metastatic efficiency (FIG. 1). This effect remained consistent across multiple passages of cells and multiple assays. The present inventors tested these cell lines for production of IL-6 and IL-8 by subjecting cell-free supernatants to ELISA (FIG. 1d), which revealed a strong correlation between tumor cell production of both of these cytokines and the cell line's capacity to colonize murine lung.

IL-6 and IL-8 Stimulate Chemokinesis and Directional Migration in OS Cells, Regardless of Metastatic Potential To demonstrate whether these highly- and poorly-metastatic cell lines maintain features that respond to these cytokines, we performed both scratch assays (wound-healing assays) and transwell migration assays to assess response. Standardized wounds created in both OS-17 and OHS cell monolayers closed more effectively when cultured in media supplemented with IL-6 and/or IL-8, demonstrating that either cytokine can stimulate chemokinesis (increased cell motility) in either cell line, irrespective of any basal production of that cytokine. These cells exhibit similar results in assays testing directional migration. Both OS-17 and OHS cells grown in the top chamber of a transwell system exhibit strong directional migration in response to chemotactic gradients of either IL-6 or IL-8.

Figure 2:
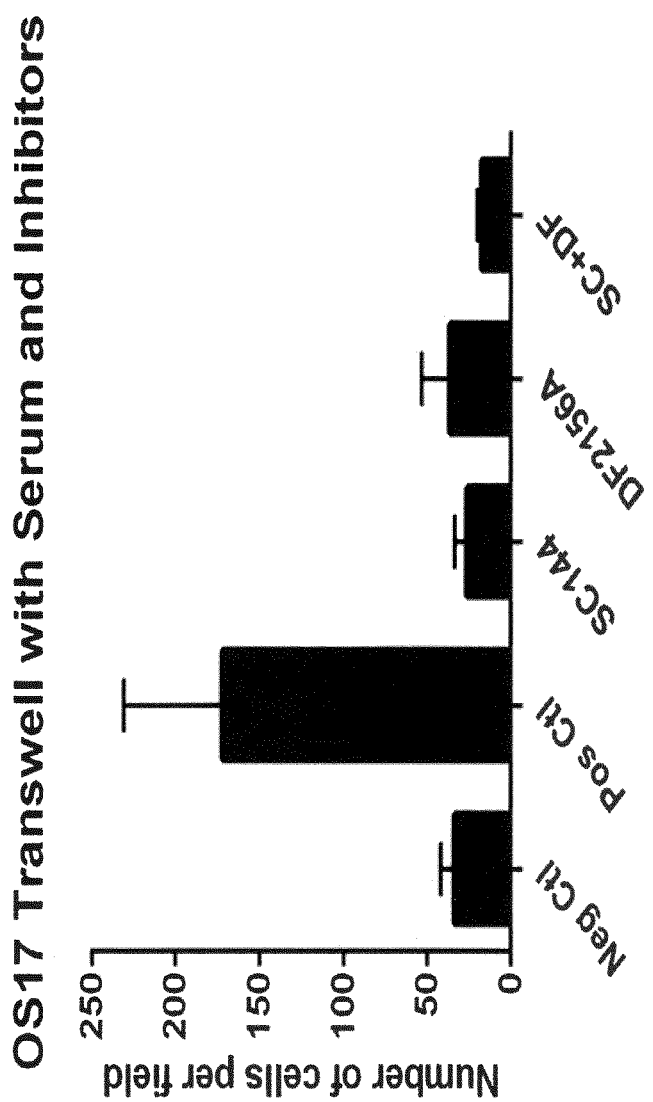
FIG. 2 shows effect of DF2156A alone or in combination with sc144 to reduce chemotactic responses to serum in OS-17 cells. OS cells were cultured on a transwell chamber membrane, then subjected transferred to a chamber containing RPMI with 2.5% FBS (pos ctl) or RPMI alone (neg ctl). Other wells containing 2.5% FBS in the bottom chamber were treated with 1 uM sc144, 10 nM DF2156A, or both. After 24 hours, top chambers were scraped clean, membranes stained and cells counted.

Effect of DF2156A Alone or in Combination with Sc144 to Prevent OS Cell Directional Migration and Invasion To determine the importance of these cytokines to OS cell migration within a much broader milieu of possible chemotactic factors, the present inventors examined the effect that IL-6 and/or IL-8 blockade might have when using serum as a chemoattractant. Both cell lines demonstrated very strong both transwell migration and invasion through a matrigel barrier in response to a chemotactic gradient of serum (FIG. 1e-f). Some decrease in the chemotactic response was evident when IL-6 or IL-8 blocking antibodies were added to the culture medium, though a much more profound effect was seen when the antibodies were combined. A more profound effect was seen in similar experiments using small molecule inhibitors of the receptors for IL-6 and IL-8 (sc144, which stimulates degradation of gp130 through a novel mechanism and DF2156A, an allosteric inhibitor of CXCR1 and CXCR2). With inhibition at the receptor level, blockade of either pathway suffices to prevent directional migration and invasion (FIG. 2), suggesting that some level of activation of these pathways, likely by non-IL-6 and non-IL-8 cytokines, is needed for OS cells to produce these behaviors. Both inhibitors significantly decreased the amount of migration of OS cells.

Example 2

Figure 3:
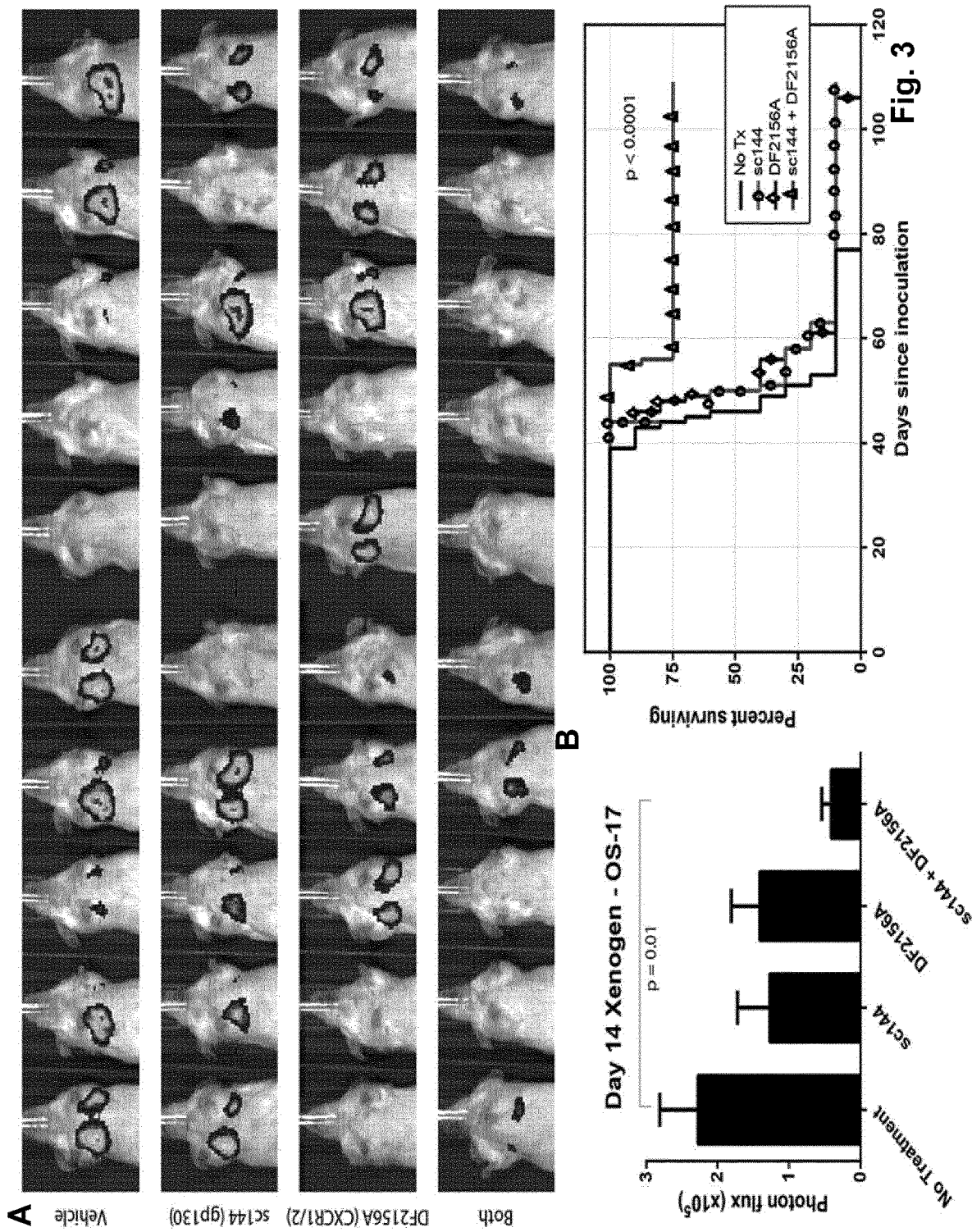
FIG. 3 shows effects of IL-6 and IL-8 pathway inhibition on metastatic lung colonization. Mice innoculated with $1\times10^6$ OS-17-luc cells were treated with pharmacologic inhibitors of IL-6 (sc144), IL-8 (DF2156A), or both. A) Bioluminescent imaging completed at 28 days post-inoculation. B) Survival analysis of the mice shown in A).
Figure 4:
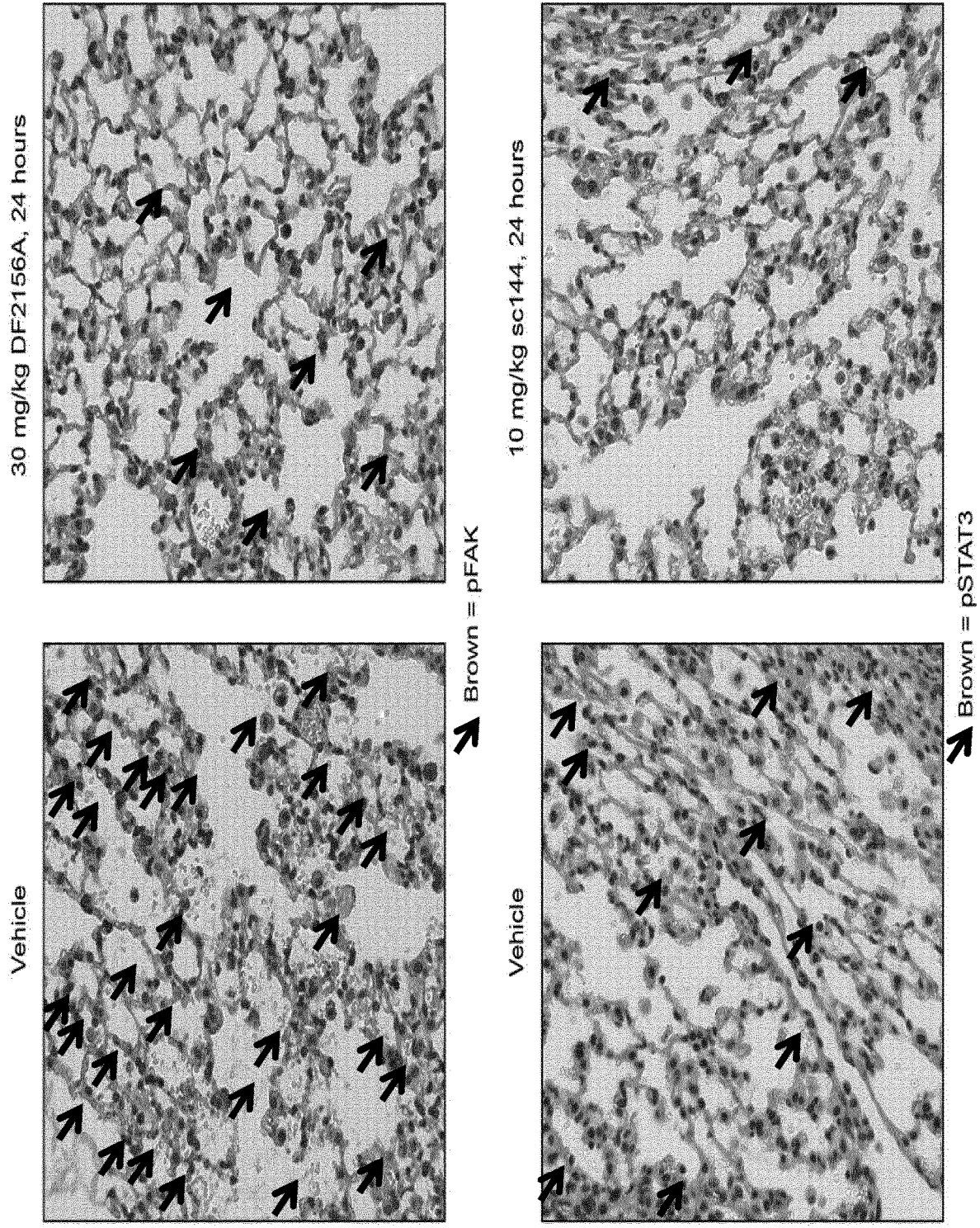
FIG. 4 shows PD analysis in lung tissue of mice treated with DF2156A and sc144. Mice treated with injections of either DF2156A or sc144 daily were euthanized 24 hours subsequent to their $14^{th}$ dose of drug. Lungs harvested from those mice were processed using standard FFPE, then sectioned and stained with IHC for either pFAK (downstream of IL-8) or pSTAT3 (downstream of IL-6). Receptor blockade reduced the amount of activation seen and the number of infiltrating cells, even at trough concentrations.

Effect of DF2156A Alone or in Combination with Sc144 in the Prevention of Lung Metastasis To evaluate the functional importance of IL-6 and IL-8 pathways to OS lung metastasis, the present inventors used the xenograft models. Balb-SCID mice inoculated via tail vein with $1\times10^6$ luciferase-labeled OS-17 cells received treatment with sc144 (the gp130 inhibitor), DF2156A (the CXCR1/2 inhibitor), or both. Mice continued to receive treatment for 42 days, after which treatment stopped. Intravital imaging for in vivo assessment of tumor burden was performed at 14 and 24 days using standard bioluminescent techniques. Bioluminescent imaging suggested markedly decreased tumor burden in the lungs of mice receiving combined therapy relative to those receiving no treatment or single-agent therapy (FIG. 3 A). Importantly, imaging did not show migration of the tumor cells into other organs, but an overall loss of bioluminescence, suggesting decreased overall survival of circulating tumor cells. Two mice from each single-agent treatment group were euthanized 24 hours after the 14$^{th}$ dose of drug to perform pharmacodynamics (PD) assessment of target inhibition. Lungs from those mice stained with IHC for either pFAK (DF2156A) or pSTAT3 (gp130) showed sustained target inhibition (i.e. sustained drug activity) at dosing trough (FIG. 4).

Following treatment, mice were then observed until demonstrating signs of clinical deterioration, either weight loss >10% or enhanced body condition score (eBCS) <8, our defined endpoints. At endpoint, mice were euthanized using approved methods and lungs were harvested, insufflated, fixed, embedded, sectioned, and stained. Survival analysis (FIG. 3 B) showed that nearly all mice receiving either no drug or single agent therapy developed lethal lung metastasis by 60 days. In particular, the mice receiving no drug developed lethal lung metastasis earlier than mice receiving single agent. Whereas most mice receiving combined therapy (gp130 inhibitor+CXCR1/2 inhibitor) remained healthy at >100 days. Mice which did not demonstrate overt lung metastasis on lung sections were censored from the survival analysis (n=2).

Example 3

Figure 5:
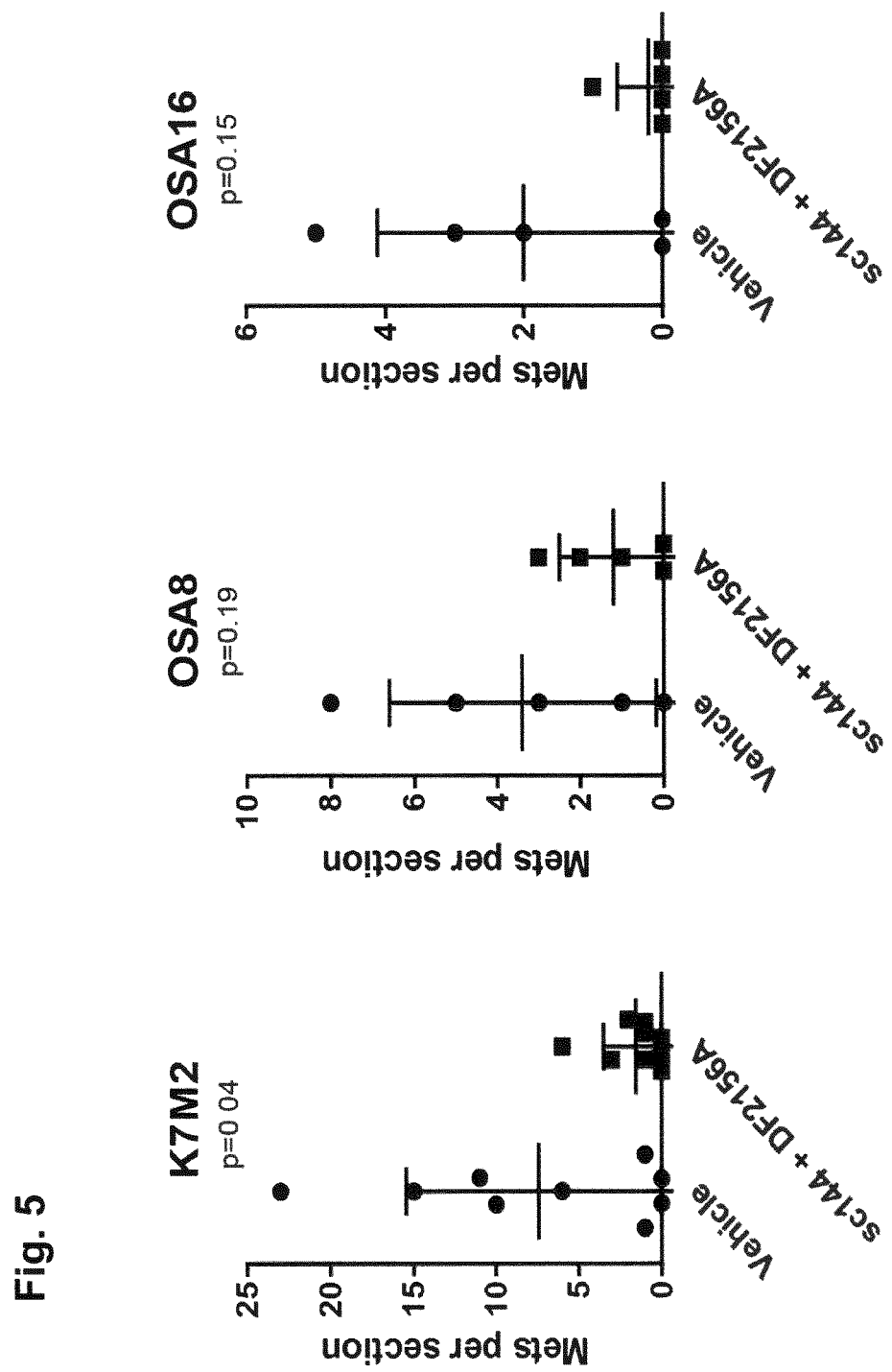
FIG. 5 shows effect of the combination DF2156A with sc144 in the prevention of lung metastasis in multiple models of OS. Subsequent to inoculation of OS cells, mice received either vehicle treatment or treatment with both sc144 and DF2156A for a period of 42 days. At the time that one mouse in either group met endpoint criteria, all mice within that study were euthanized and lungs harvested, metastatic lesions counted.

Effect of the Combination DF2156A with Sc144 in the Prevention of Lung Metastasis in Multiple Models of OS To ensure that the results obtained in these studies were broadly applicable and not unique to immunodeficient xenografts or to OS-17 cells, the present inventors repeated the treatment-related experiments using a number of different models. These included a syngeneic, immunocompetent model using a cell line derived from a spontaneously-arising OS in a Balb/c mouse (K7M2), xenograft models of canine OS (OSCA-8 and OSCA-16), and additional xenograft models of human OS (143B). Mice inoculated with tumor cells were treated with either no drug or combined sc144 and DF2156A for 42 days. At the time that at least one mouse from any group (any cell line) reached endpoint with confirmed lung metastasis, all mice from that group were euthanized, lungs harvested, and metastatic lesions quantified. The ability of dual gp130-CXCR1/2 inhibition to prevent the development of metastatic lung lesions remained consistent across models (FIG. 5).

The invention claimed is:
1. A method of preventing and/or treating lung metastasis of osteosarcoma, the method comprising administering to a subject in need thereof a therapeutically effective amount of an IL-8 inhibitor, which is a 2-phenyl-propionic acid derivative compound of formula (II)

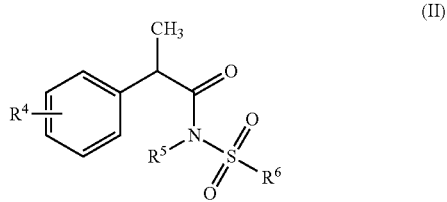

(II)

or a pharmaceutically acceptable salt thereof, wherein:
$R^4$ is linear or branched $C_1$-$C_6$ alkyl, benzoyl, phenoxy, trifluoromethanesulfonyloxy;
$R^5$ is H or linear or branched $C_1$-$C_3$ alkyl; and
$R^6$ is linear or branched $C_1$-$C_6$ alkyl or trifluoromethyl.

2. A method of preventing and/or treating lung metastasis of osteosarcoma, the method comprising administering to a subject in need thereof a therapeutically effective amount of an IL-8 inhibitor, which is a 2-phenly-propionic acid derivative compound of formula (III)

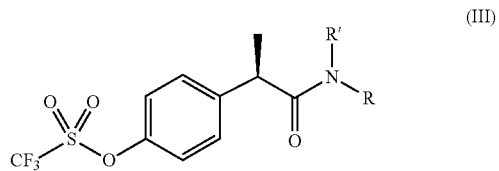

(III)

or pharmaceutically acceptable salts thereof, wherein
R' is hydrogen; and
R is a residue of formula SO$_2$Ra wherein Ra is linear or branched $C_1$-$C_4$ alkyl or halo $C_1$-$C_3$ alkyl.

3. The method according to claim 1, wherein the chiral carbon atom of the phenylpropionic group is in the R configuration.

4. The method according to claim 1, wherein said compound or said pharmaceutically acceptable salt thereof is selected from R-(−)-2-(4-isobutylphenyl)propionyl methanesulfonamide and pharmaceutically acceptable salts thereof.

5. The method according to claim 1, wherein said compound or said pharmaceutically acceptable salt thereof is selected from R(−)-2-(4-trifluoromethanesulfonyloxy)phenyl]-N-methanesulfonyl propionamide and pharmaceutically acceptable salts thereof.

6. The method of claim 1, wherein the IL-8 inhibitor is part of a pharmaceuticaly composition comprising one or more pharmaceutically acceptable excipients and/or diluents, the method comprising administering the pharmaceutical composition to the subject.

7. The method according to claim 6, wherein the pharmaceutical composition further comprises one or more of (a) at least one IL-6 inhibitor and (b) at least one gp130 inhibitor.

8. The method according to claim 6, wherein the pharmaceutical composition further comprises at least one chemotherapeutic agent selected from the group consisting of doxorubicin, cisplatin, methotrexate, ifosfamide, epirubicin, etoposide, cyclophosphamide, vincristine, and actinomycin D.

9. A method of preventing and/or treating lung metastasis of osteosarcoma, the method comprising administering a product or a kit to a patient in need thereof, the product or kit comprising:
(A) an IL-8 inhibitor according to claim 1, or a pharmaceutical composition comprising said IL-8 inhibitor and one or more pharmaceutically acceptable excipients and/or diluents; and
(B) one or more of at least one IL-6 inhibitor and at least one gp130 inhibitor;
(A) and (B) being two separate formulations for simultaneous, separate or sequential use.

10. A method of preventing and/or treating lung metastasis of osteosarcoma, the method comprising administering a product or a kit to a patient in need thereof, the product or kit comprising:
- (A') an IL-8 inhibitor according to claim 1, or a pharmaceutical composition comprising said IL-8 inhibitor and one or more pharmaceutically acceptable excipients and/or diluents; and
- (B') at least one chemotherapeutic agent selected from the group consisting of doxorubicin, cisplatin, methotrexate, ifosfamide, epirubicin, etoposide, cyclophosphamide, vincristine, and actinomycin D;
- (A') and (B') being two separate formulations for simultaneous, separate or sequential use.

11. The method of claim 1, further comprising the administration of an IL-6 inhibitor and/or a GP130 inhibitor.

12. The method according to claim 2, wherein the chiral carbon atom of the phenylpropionic group is in the R configuration.

13. The method according to claim 2, wherein said compound or said pharmaceutically acceptable salt thereof is selected from R(−)-2-(4-trifluoromethanesulfonyloxy) phenyl]-N-methanesulfonyl propionamide and pharmaceutically acceptable salts thereof.

14. The method of claim 2, wherein the IL-8 inhibitor is part of a pharmaceutical composition comprising one or more pharmaceutically acceptable excipients and/or diluents, the method comprising administering the pharmaceutical composition to the subject.

15. The method according to claim 14, wherein the pharmaceutical composition further comprises one or more of (a) at least one IL-6 inhibitor and (b) at least one gp130 inhibitor.

16. The method according to claim 14, wherein the pharmaceutical composition further comprises at least one chemotherapeutic agent selected from the group consisting of doxorubicin, cisplatin, methotrexate, ifosfamide, epirubicin, etoposide, cyclophosphamide, vincristine, and actinomycin D.

17. A method of preventing and/or treating lung metastasis of osteosarcoma, the method comprising administering a product or a kit to a patient in need thereof, the product or kit comprising:
- (A) an IL-8 inhibitor according to claim 2, or a pharmaceutical composition comprising said IL-8 inhibitor and one or more pharmaceutically acceptable excipients and/or diluents; and
- (B) one or more of at least one IL-6 inhibitor and at least one gp130 inhibitor;
- (A) and (B) being two separate formulations for simultaneous, separate or sequential use.

18. A method of preventing and/or treating lung metastasis of osteosarcoma, the method comprising administering a product or a kit to a patient in need thereof, the product or kit comprising:
- (A') an IL-8 inhibitor according to claim 2, or a pharmaceutical composition comprising said IL-8 inhibitor and one or more pharmaceutically acceptable excipients and/or diluents; and
- (B') at least one chemotherapeutic agent selected from the group consisting of doxorubicin, cisplatin, methotrexate, ifosfamide, epirubicin, etoposide, cyclophosphamide, vincristine, and actinomycin D;
- (A') and (B') being two separate formulations for simultaneous, separate or sequential use.

19. The method of claim 2, further comprising the administration of an IL-6 inhibitor and/or a GP130 inhibitor.

\* \* \* \* \*